United States Patent [19]

Himizu et al.

[11] 4,113,873
[45] Sep. 12, 1978

[54] 8-AZAPROSTANOIC ACID DERIVATIVES

[75] Inventors: Junichi Himizu, Urawa; Shoichi Harigaya, Kawasaki; Shigeyoshi Saijo, Urawa; Masao Wada, Warabi; Katsuyuki Noguchi, Kitamoto; Osasi Takaiti, Tokyo, all of Japan

[73] Assignee: Tanabe Seiyaku Co. Ltd., Osaka, Japan

[21] Appl. No.: 793,920

[22] Filed: May 5, 1977

Related U.S. Application Data

[63] Continuation-in-part of Ser. No. 733,006, Oct. 15, 1976, abandoned, which is a continuation-in-part of Ser. No. 677,327, Apr. 15, 1976, abandoned.

[30] Foreign Application Priority Data

Apr. 26, 1975 [JP] Japan .................................. 50-50907
Apr. 30, 1975 [JP] Japan .................................. 50-52930
Oct. 9, 1976 [JP] Japan ................................. 51-121698
Oct. 9, 1976 [JP] Japan ................................. 51-121699

[51] Int. Cl.$^2$ .................... A61K 31/40; C07D 207/26
[52] U.S. Cl. ........................... 424/274; 260/326.43; 260/326.45
[58] Field of Search ................ 260/326.43; 424/274

[56] References Cited

U.S. PATENT DOCUMENTS 3,925,399  8/1976  DeFranco et al. ................ 260/326.2

FOREIGN PATENT DOCUMENTS 2,618,176  4/1976  Fed. Rep. of Germany.
511,460  8/1976  Japan.
511,461  8/1976  Japan.
51,127,068  5/1976  Japan.

Primary Examiner—Donald G. Daus
Assistant Examiner—Lisa Jones
Attorney, Agent, or Firm—Bierman & Bierman

[57] ABSTRACT

Novel 8-azaprostanoic acid derivatives and processes for preparing the same are disclosed. Said 8-azaprostanoic acid derivatives are shown by the formula:

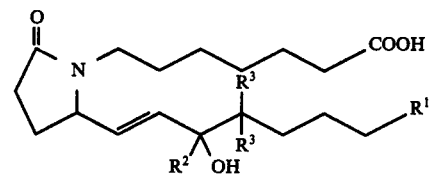

wherein $R^1$ is hydrogen or alkyl of 2 to 6 carbon atoms, $R^2$ is hydrogen or methyl and $R^3$ is hydrogen, or $R^1$ is methyl when $R^2$ is hydrogen and $R^3$ is methyl. They exhibit Prostaglandin-like activities and are useful as bronchodilators, stimulating agents for childbirth, abortion or labor, and/or for the treatment of gastro-intestinal disorders.

12 Claims, No Drawings

8-AZAPROSTANOIC ACID DERIVATIVES

This application is a continuation-in-part of U.S. Ser. No. 733,006, filed Oct. 15, 1976 now abandoned, which is a continuation-in-part of Ser. No. 677,327, filed on Apr. 15, 1976, now abandoned.

This invention relates to a novel 8-azaprostanoic acid derivative and a process for preparing the same. More particularly, it relates to a compound of the formula:

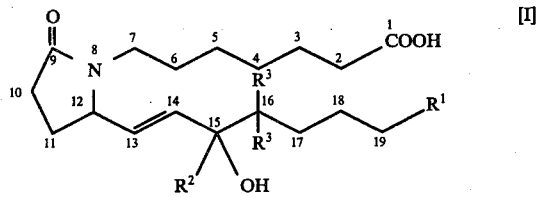

wherein $R^1$ is hydrogen or alkyl of 2 to 6 carbon atoms, $R^2$ is hydrogen or methyl and $R^3$ is hydrogen; or $R^1$ is methyl when $R^2$ is hydrogen and $R^3$ is methyl. Pharmaceutically acceptable salts of the compound [I] are also included within the scope of the present invention.

Prostaglandins have been known to show a wide variety of interesting biological effects (see, for example, Advances in the Biosciences Vol. 9, International conference on prostaglandins, ed. Pergamon Press, Vieweg, 1973), and 8 different series of prostaglandins (A,B,C,E,E,Fα,G & H) have been so far identified in various sources such as seminal fluid, kidney, lung, central nerves system and so forth. Moreover, the synthesis of heterocyclic derivatives of prostaglandins and pharmacological properties thereof have been reported recently. For example, Himizu et al prepared 10-oxa-prostanoic acid derivatives such as 15(S)-hydroxy-9-oxo-13,14(trans)-didehydro-10-oxaprostanoic acid and at the same time found that they are useful for the treatment of gastro-intestinal disorders or as stimulating agents for childbirth (U.S. Pat. No. 3787448). R. M. Scriber discloses that 8,12-diazaprostanoic acid derivatives such as sodium 7-[3'-oxo-1'-(3'-hydroxyoctyl-pyrazolidine-2-yl]heptanoate and ethyl 7-[3'-oxo-2'-(3'-hydroxy-n-octyl)-pyrazolidine-1'-yl]heptanoate show prostaglandin-like activities or antagonistic effects against prostaglandins (Japanese patent application No. 51562/1973, laid open to the public without examination under No. 61164/1974). Further, the synthesis of 9- or 11-oxa-prostaglandins and 9-thiaprostaglandins have been reported by I. Vlattas et al in Tetrahedron Letters No. 48, pp 4267 (1974) and ibid. No. 51/52, pp 4451 - 4462(1974).

We have now found that the compound [I] shows various prostaglandin-lie biological activities and is useful in the treatment where the use of prostaglandins is indicated. For example, the compound [I] of the invention shows a potent bronchodilating activity for a long period of time and is useful as a bronchodilator. When the bronchodilating activity is estimated by the preventive effect against histamineinduced bronchoconstriction after the intravenous injection thereof(animals used: guinea pigs), dl-20-methyl-15α-hydroxy-13,14(trans)-didehydro-9-oxo-8-azaprostanoic acid at the dose of 3 μg/kg(i.v.) shows the maximum level of bronchoconstriction for about 20 minutes or longer. Moreover, when estimated under the same conditions as above, 1-20-ethyl-15α-hydroxy-13,14(trans)-didehydro-9-oxo-8-azaprostanoic acid shows the bronchodilating activity 10 times or more stronger than that of Prostaglandin $E_1$ and said activity of the former compound at the dose of 3 μg/kg(i.v.) lasts for about one hour at its maximum level. The compound [I] of the invention may also be useful as a stimulating agent for the child-birth, abortion or labor or as a hypotensive agent. For example, dl-20-methyl-15 ξ-hydroxy-13,14(trans)-didehydro-9-oxo-8-azaprostanoic acid enhances spontaneous contraction of the uterus, and dl-15 ξ,20-dimethyl-15 ξ-hydroxy-13,14(trans)-didehydro-9-oxo-8-azaprostanoic acid can increase the frequency of uterine rhythmic movement without decrease in contractile force. In addition, while 1-20-ethyl-15α-hydroxy-13,14(trans)-didehydro-9-oxo-8-azaprostanoic acid shows a long-lasting bronchodilating effect at the dose of 0.3 μg/kg(i.d.), it also shows a blood pressure-lowering activity when administered to rats at a dose of not less than 30 μg/kg(i.d.).

Further, the compound [I] may be useful for the treatment of gastro-intestinal disorders or gastric ulcers. It shows an increasing effect upon the propulsive motility of the intestine as well as the preventive effects against the spontaneous or peristaltic motility of the stomach. When the intestinal motility of mice is estimated by a modified Van Liere's method, for example, dl-16,16-dimethyl-15 ξ -hydroxy-13,14(trans)-didehydro-9-oxo-8-azaprostanoic acid at the dose of 30 μg/kg(i.p.) or 1-20-methyl-15α-hydroxy-13,14(trans)-didehydro-9-oxo-8-azaprostanoic acid at the dose of 10 μg/kg(i.p.) increase the propulsive motility of intestine about 1.5 to 1.7 times as high as that of a control group. The compound [I] may further show a preventive effect against secretion of gastric acid.

The toxicity of the compound [I] is low. For example, no mice die when dl-20-methyl-15α-hydroxy-13,14(trans)-didehydro-9-oxo-8-azaprostanoic acid is injected intraperitoneally to mice at the dose of 300 mg/kg.

The compound [I] of the present invention can be used for pharmaceutical use either as the free acid or a salt thereof. Pharmaceutically acceptable salts of the compound [I] include, for example, alkali or alkali earth metal salts (e.g., sodium, potassium and calcium salts), quaternary ammonium salts (e.g., ammonium and tetramethylammonium salts) and organic amine salts (e.g., cyclopentylamine, benzylamine, triethanolamine and monoethanol amine salts). The compound [I] may be administered in the form of a pharmaceutical preparation suitable for enteral or parenteral administration or inhalation in the case of bronchodilators. The pharmaceutical preparation may be a solid dosage form (e.g., a tablet, a pill, a capsule or pulvers) or a liquid dosage form (e.g., a solution, a suspension or an emulsion). Further, the compound [I] may be used in conjunction or admixture with a pharmaceutical excipient which is suitable for enteral or parenteral administration or for inhalation. Suitable excipients may include, for example, gelatin, lactose, glucose, starch, vegetable oil and so forth.

According to the present invention, the compound [I] in which $R^2$ is hydrogen can be prepared by condensing a 1-alkoxycarbonylhexyl-5-formyl-2-pyrrolidone of the formula:

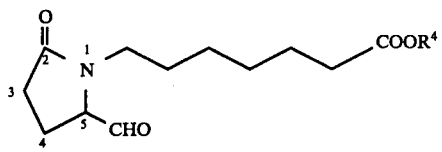

[II]

wherein R⁴ is lower alkyl, with a Wittig reagent of the formula:

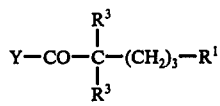

wherein R¹ and R³ are the same as defined above, Y is a group of the formula: $(R^5O)_2OPCH_2$— or $(C_6H_5)_3P=CH$— and R⁵ is lower alkyl, to give a compound of the formula:

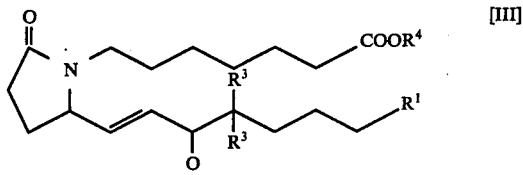

[III]

wherein R¹, R³ and R⁴ are the same as defined above, reducing the compound [III] at the carbonyl group thereof to give a compound of the formula:

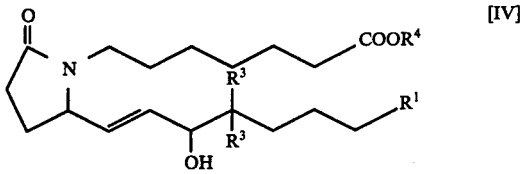

[IV]

wherein R¹, R³ and R⁴ are the same as defined above, and then hydrolyzing the compound [IV]. On the other hand, the compound [I] in which R² is methyl can be prepared by reacting the compound [III] with a Grignard reagent of the formula:

wherein X is halogen, to give a compound of the formula:

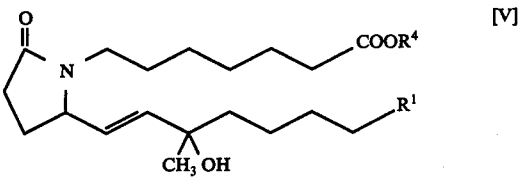

[V]

wherein R¹ and R⁴ are the same as defined above, and then hydrolyzing the compound [V].

The 5-formyl-2-pyrrolidone derivative [II] has an asymmetric carbon atom at the 5th-position thereof and can exist in the form of two stereoisomers, i.e., d- and l-isomers. Either the optically active isomers or the racemic mixture (i.e., dl-modification) thereof can be employed in the present invention. Moreover, all the reactions of the present invention can be carried out without racemization. When the optically active or racemic (i.e., d-, l- or dl-) 5-formyl-2-pyrrolidone derivative [II] is employed as the starting material, therefore, the intermediate products [III] through [V] as well as the end product [I] can be obtained as the corresponding optically active or racemic (i.e., d-, l- or dl-) compound.

The condensation of the 1-alkoxycarbonylhexyl-5-formyl-2-pyrrolidone [II] with the Wittig reagent can be conducted in a solvent. Dimethoxyethane is suitable as the reaction solvent. It is preferred to carry out the reaction at a temperature of 0° to 30° C. in an inert gas such as nitrogen gas. The reaction may be carried out either in the presence or absence of an alkali metal hydride. Lithium hydride, sodium hydride and potassium hydride may be preferably employed as the alkali metal hydride.

The reduction of the compound [III] is readily accomplished. For example, it is carried out by treating the compound [III] with a metal borohydride in a solvent. Lithium borohydride, sodium borohydride, potassium borohydride and zinc borohydride are preferably employed as the metal borohydride. Methanol, ethanol and isopropanol are suitable as the reaction solvent. It is preferred to carry out the reaction at a temperature of −30° to 25° C., especially −15° to 5° C.

The reaction of the compound [III] with the Grignard reagent is accomplished by conventional methods. For example, it is carried out at a temperature below −20° C. in a solvent. Ethylether, tetrahydrofuran and dioxane are suitable as the reaction solvent. Preferred examples of the halogen atom shown by the symbol "X" include bromine and iodine.

Each one of the compounds [IV] and [V] thus obtained is composed of the stereoisomers which differ in the steric configuration of the hydroxy group at the 15th-position thereof and, if required, these isomers may be readily separated into each components by silica gel chromatography using ethylacetatebenzene-methanol or ethylacetate-benzene as a solvent. Throughout the specification and claims, the more polar isomer or component (i.e., the one which is more strongly absorbed on silica gel) is designated as "15α-isomer" and the less polar isomer or component (i.e., the one which is less strongly absorbed on silica gel) as "15β-isomer" by analogy with the chromatographic behaviors of the esters of natural Prostaglandins. In carrying out the silica gel chromatography the 15β-isomer is always eluted in early fractions and the 15β-isomer in late fractions, due to the difference of polarity between these components. Further, if required, one of these components (i.e., 15α- and 15β-isomers) of the compound [IV] may be converted to the compound [III] in order to use the former again as the starting material in the synthesis of the another component. The conversion of the compound [IV] into the compound [III] may be carried out by a conventional oxidation reaction, for example, by treating the former with anhydrous chromic acid-pyridine complex at room temperature in a solvent.

The hydrolysis of the compounds [IV] and [V] can be carried out by treating them with an alkali metal hydroxide. It is preferred to carry out the reaction at a temperature of 0° to 30° C. in a solvent. Preferred examples of the alkali metal hydroxide include sodium hydroxide and potassium hydroxide. Lower alkanols (e.g., methanol, ethanol) or aqueous mixtures thereof may be suitable as the reaction solvent. Either one of the 15α- and 15β-isomers of the compound [IV] or [V] may be employed in the above-mentioned hydrolysis, and the compound [I] is obtained as the 15α- or 15β-isomer from the corresponding isomer (i.e., the 15α- or 15β-isomer) of the compound [IV] or [V]. Alternatively, the mixture of these isomers of the compound [IV] or [V] may be employed in this reaction.

The starting compound [II] of the present invention is a novel compound. The racemic (i.e., dl-) 1-alkoxycarbonylhexyl-5-formyl-2-pyrrolidone [II] can be prepared, for example, by condensing racemic N-trimethylsilyl 5-acetoxymethyl-2-pyrrolidone with 6-methoxycarbonyl-2-hexynyl iodide at 70° C. in the presence of potassium carbonate in a solvent (e.g., dimethoxyethane) under stirring; hydrolyzing the resultant racemic 1-(6-methoxycarbonyl-2-hexynyl)-5-acetoxymethyl-2-pyrrolidone with an alkali metal hydroxide (e.g., sodium hydroxide, potassium hydroxide) at room temperature in a solvent (e.g., aqueous methanol) to give racemic 1-(6-carboxyl-2-hexynyl)-5-hydroxymethyl-2-pyrrolidone; hydrogenating the racemic 5-hydroxymethyl-2-pyrrolidone in the presence of a catalyst (e.g., palladium-carbon, platinum dioxide) under a hydrogen atmosphere in a solvent (e.g., ethylacetate); esterifying the resultant racemic 1-(6-carboxyhexyl)-5-hydroxymethyl-2-pyrrolidone with an alkanol of the formula: $R^3$-OH, wherein $R^3$ is the same as defined above, at room temperature in the presence of a catalyst (e.g., hydrochloric acid, sulfuric acid, p-toluenesulfonic acid) in a solvent (e.g., methanol, ethanol) to give a racemic 1-(6-alkoxycarbonylhexyl)-5-hydroxymethyl-2-pyrrolidone; and then treating the 5-hydroxymethyl-2-pyrrolidone with an oxidizing agent (e.g., dimethylsulfoxide-dicyclohexylcarbodiimide, N-bromosuccinimide-dimethylsulfide, dimethylsulfoxide-acetic acid anhydride, anhydrous chromic acid-pyridine complex) under a nitrogen atmosphere at room temperature or under ice-cooling. Alternatively, the optically active or racemic (i.e., d-, l- or dl-) 1-alkoxycarbonylhexyl-5-formyl-2-pyrrolidone [II] may be prepared by condensing an optically active or racemic 5-hydroxymethyl-2-pyrrolidone with vinylethyl ether in the presence of a small amount of an acid (e.g., hydrochloric acid, hydrobromic acid, trichloroacetic acid) in a solvent (e.g., chloroform) to give optically active or racemic 5-[1-(ethoxy)ethoxymethyl]-2-pyrrolidone; condensing an alkali metal salt (e.g., sodium salt) of said pyrrolidone with a lower alkyl 7-bromo-n-heptanoate in the presence of potassium iodide in an inert gas (e.g., nitrogen gas) atmosphere at 50° C. in a solvent (e.g., dimethylformamide); treating the resultant optically active or racemic 5-[1-(ethoxy)ethoxymethyl]-1-(6-lower alkoxycarbonylhexyl)-2-pyrrolidone with a strong acid (e.g., p-toluenesulfonic acid) at room temperature in a solvent (e.g., methanol) to give an optically active or racemic 1-(6-lower alkoxycarbonylhexyl)-5-hydroxymethyl-2-pyrrolidone; and then treating the 5-hydroxymethyl-2-pyrrolidone with an oxidizing agent (e.g., dimethylsulfoxide-dicyclohexylcarbodiimide, anhydrous chromic acid-pyridine complex) under a nitrogen atmosphere at room temperature or under ice-cooling.

Practical and presently-preferred embodiments of the present invention are illustratively shown in the following Examples. Throughout the specification and claims the term "lower alkyl" refers to alkyl groups having one to five carbon atoms.

EXAMPLE 1

(1) A solution of 675 mg of dl-1-(6-methoxycarbonyl-2-hexynyl)-5-acetoxymethyl-2-pyrrolidone in 7 ml of methanol is added to 7 ml of an aqueous 5% sodium hydroxide solution under ice-cooling. The mixture is stirred at room temperature for 18 hours. After the reaction, the mixture is evaporated under reduced pressure to remove methanol. Water is added to the residue, and the aqueous solution is washed with ether. Then, the aqueous solution is acidified with 20% hydrochloric acid. The solution is saturated with ammonium sulfate and extracted with ethylacetate. The extract is washed with water, dried and then evaporated to remove solvent. The residue thus obtained is recrystallized from ethylacetate. dl-1-(6-Carboxy-2-hexynyl)-5-hydroxymethyl-2-pyrrolidone is obtained as colorless needles. Yield: 497 mg. M.p. 100°–101° C.

(2) 497 mg of dl-1-(6-carboxy-2-hexynyl)-5-hydroxymethyl-2-pyrrolidone are dissolved in a mixture of 10 ml of ethylacetate and 2 ml of methanol. A mixture of 400 mg of 10% palladium-carbon and 45 ml of ethylacetate is shaken in hydrogen gas, and the solution of the above-mentioned 2-pyrrolidone compound is added thereto. Then, the mixture is further shaken in hydrogen gas until 160 ml of hydrogen is absorbed therein. The catalyst is removed by filtration, and the filtrate is evaporated under reduced pressure to remove solvent. The residue thus obtained is recrystallized from ethylacetate. dl-1-(6-Carboxyhexyl)-5-hydroxymethyl-2-pyrrolidone are obtained as colorless scales. Yield: 454 mg. M.p. 79°–80° C.

(3) 0.31 g of p-toluenesulfonic acid is added to 20 ml of methanol containing one g of dl-1-(6-carboxyhexyl)-5-hydroxymethyl-2-pyrrolidone. The addition is carried out under ice-cooling. The solution is stirred at room temperature for 4.5 hours. After the reaction, the solution is evaporated to remove solvent. The residue is dissolved in ethylacetate, and the ethylacetate solution is washed with an aqueous sodium bicarbonate solution and water, successively. The solution is dried and then evaporated to remove solvent. dl-1-(6-Methoxycarbonylhexyl)-5-hydroxymethyl-2-pyrrolidone is obtained as pale yellow oil. Yield: 0.86 g (4) A solution of 0.34 ml of dimethylsulfide in one ml of toluene is added dropwise to 17 ml of a toluene solution containing 596 mg of N-chlorosuccinimide. The addition is carried out in nitrogen gas under ice-cooling. The solution is stirred at the same temperature for one hour. A solution of 430 mg of dl-1-(6-methoxycarbonylhexyl)-5-hydroxymethyl-2-pyrrolidone in one ml of toluene is added dropwise thereto, and the mixture is stirred at the same temperature for 12.5 hours. Then, a solution of 340 mg of triethylamine in one ml of toluene is added dropwise to the mixture, and said mixture is further stirred at the same temperature for 30 minutes. After the reaction, ether is added to the mixture. The mixture is washed with one % hydrochloric acid saturated with ammonium sulfate, washed with water, dried and then evaporated to remove solvent. The residue thus obtained is purified by thin layer chromatography [Silica gel; Solvent: ethylacetate-methanol (8:1)]. dl-1-(6-Methoxycarbonylhexyl)-5-formyl-2-pyrrolidone is obtained as pale yellow oil. Yield: 290 mg.

IR spectrum $\nu_{max.}^{liq.}$(cm$^{-1}$): 1735(ester), 1720(aldehyde), 1600 (lactam)

NMR spectrum ppm(CDCl₃): 3.69(3H, S, —OC$\underline{H}$₃), 9.70(1H, m, —C$\underline{H}$O)

Mass analysis
m/e: 256(M⁺ + 1), 255(M⁺)

EXAMPLE 2

(1) 4 g of dl-5-hydroxymethyl-2-pyrrolidone are dissolved in 20 ml of chloroform, and 0.1 g of trichloroacetic acid and 16 ml of vinylethylether are added thereto. The solution is stirred at room temperature for 4 hours. After the reaction, the solution is cooled with ice-water, and washed with an aqueous sodium bicarbonate solution. The washings is extracted with chloroform. Then, the reaction solution and chloroform extract are combined, and the combined mixture is washed with water saturated with ammonium sulfate, dried and evaporated to remove solvent. The residue thus obtained is distilled under reduced pressure. dl-5-[1-(Ethoxy)ethoxymethyl]-2-pyrrolidone is obtained as pale yellow oil. Yield: 6.45 g. B.p. 137°–138° C./1.5 mmHg (2) A solution of 5.98 g of dl-5-[1-(ethoxy)ethoxymethyl]-2-pyrrolidone in 8 ml of dimethylformamide is added gradually to a mixture of 40 ml of dimethylformamide, 1.24 g of 65% sodium hydride (an oil dispersion; washed with n-hexane) and 6.41 g of potassium iodide. The addition is carried out in nitrogen gas under ice-cooling and stirring. The solution is stirred at room temperature for 2 hours and then at 50° C. for 20 minutes. After the solution is cooled to room temperature, 8.6 g of methyl 7-bromo-n-heptanoate are added thereto, and the mixture is stirred at 50° C. for 2 days. Insoluble materials are filtered off. The filtrate is evaporated at 60° to 75° C. under reduced pressure (4 mmHg) to remove solvent. The residue obtained is mixed with ether and an aqueous saturated ammonium sulfate solution, and the mixture is shaken. Then, the organic solvent layer is separated from the mixture, and the aqueous layer is extracted with ether. The organic solvent layer and ether extract are combined, washed with water saturated with ammonium sulfate, dried and then evaporated to remove solvent. The residue thus obtained is purified by silica gel chromatography [Solvent: ethylacetate-methanol (20:1)]. dl-5-[1-(Ethoxy)ethoxymethyl]-1-(6-methoxycarbonylhexyl)-2-pyrrolidone is obtained as yellowish brown oil. Yield: 8.16 g (3) A solution of 8.16 g of dl-5-[1-(ethoxy)ethoxymethyl]-1-(6-methoxycarbonylhexyl)-2-pyrrolidone and 0.92 g of p-toluenesulfonic acid in 92 ml of methanol is stirred at room temperature for 2.5 hours. The solution is evaporated to remove solvent. The residue is dissolved in ethylacetate, and the ethylacetate solution is washed with an aqueous sodium bicarbonate solution and an aqueous saturated ammonium sulfate solution, successively. Then, the solution is dried and evaporated to remove solvent. The residue thus obtained is distilled under reduced pressure. dl-1-(6-Methoxycarbonylhexyl)-5-hydroxymethyl-2-pyrrolidone is obtained as colorless oil. Yield: 5.74 g B.p. 190°–192° C./0.08 mmHg (4) 16.5 g of chromium trioxide are added to a mixture of 24 ml of pyridine and 420 ml of dichloromethane at 25° C. under a nitrogen gas atmosphere. The mixture is stirred at room temperature for 15 minutes. A solution of 6.5 g of dl-1-(6-methoxycarbonylhexyl)-5-hydroxymethyl-2-pyrrolidone in 30 ml of dichloromethane is added to the mixture at room temperature. Then, the mixture is stirred at room temperature for 30 minutes, 11.5 ml of isopropanol are added thereto, and said mixture is further stirred at room temperature for 10 minutes. After the reaction, the dichloromethane layer is collected by decantation. The residue is washed with 50 ml of dichloromethane under stirring vigorously, and the dichloromethane layer is again collected by decantation. Further, the residue is washed twice with 50 ml of ether and the ether layers are collected by decantation. After the dichloromethane and ether layers are combined, 33 g of silica gel are added thereto, and said mixture is evaporated to remove solvent. The silica gel powder thus obtained is placed on the column of 70 g of silica gel, and eluted with ethylacetate-methanol(9:1). dl-1-(6-Methoxycarbonylhexyl)-5-formyl-2-pyrrolidone is obtained as pale yellow oil. Yield: 4.78 mg

EXAMPLE 3

(1) 17 g of l-5-hydroxymethyl-2-pyrrolidone, 0.43 g of trichloroacetic acid and 71 ml of vinylethylether are treated in the same manner as described in Example 2-(1). l-5-[1-(Ethoxy)ethoxymethyl]-2-pyrrolidone is obtained as pale yellow oil. Yield: 24.5 g B.p. 152°–154° C./4 mmHg $[\alpha]_D^{25}$ −22.6°(C = 2, ethanol)

(2) 21.0 g of l-5-[1-(ethoxy)ethoxymethyl]-2-pyrrolidone, 4.47 g of 65% sodium hydride, 22.46 g of potassium iodide and 30.3 g of methyl 7-bromo-n-heptanoate are treated in the same manner as described in Example 2-(2). l-5-[1-(Ethoxy)ethoxymethyl]-1-(6-methoxycarbonylhexyl)-2-pyrrolidone is obtained as colorless oil. Then, a mixture of said pyrrolidone compound and 1.5 g of p-toluenesulfonic acid are treated in the same manner as described in Example 2-(3). l-1-(6-Methoxycarbonylhexyl)-5-hydroxymethyl-2-pyrrolidone is obtained as colorless oil. Yield. 22.0 g B.p. 200°–203° C./0.1 mmHg $[\alpha]_D^{27.5}$ −9.4°(C = 2, ethanol)

(3) 2.88 g of l-1-(6-methoxycarbonylhexyl)-5-hydroxymethyl-2-pyrrolidone, 7.0 g of chromium trioxide and 11.3 ml of pyridine are treated in the same manner as described in Example 2-(4). l-1-(6-Methoxycarbonylhexyl)-5-formyl-2-pyrrolidone is obtained as faintly yellow oil. Yield: 1.54 g $[\alpha]_D^{22}$ −2.3°(C = 2.04, ethanol)

EXAMPLE 4

(1) 3.65 g of d-5-hydroxymethyl-2-pyrrolidone, 0.1 g of trichloroacetic acid and 16 ml of vinylethylether are treated in the same manner as described in Example 2-(1). d-5-[1-(Ethoxy)ethoxymethyl]-2-pyrrolidone is obtained as pale yellow oil. Yield: 5.45 g B.p. 119°–121° C./0.2 mmHg $[\alpha]_D^{24.5}$ +20.8°(C = 2, ethanol)

(2) 2.0 g of d-5-[1-(ethoxy)ethoxymethyl]-2-pyrrolidone, 0.42 g of 65% sodium hydride, 2.13 g of potassium iodide and 2.87 g of methyl 7-bromo-n-heptanoate are treated in the same manner as described in Example 2-(2). d-5-[1-(Ethoxy)ethoxymethyl]-1-(6-methoxycarbonylhexyl)-2-pyrrolidone is obtained. Yield 5.65 g(crude product)

(3) 5.65 g of d-5-[1-(ethoxy)ethoxymethyl]-1-(6-methoxycarbonylhexyl)-2-pyrrolidone and 0.3 g of p-toluenesulfonic acid are treated in the same manner as described in Example 2-(3). d-1-(6-Methoxycarbonylhexyl)-5-hydroxymethyl-2-pyrrolidone is obtained as colorless oil. Yield: 1.42 g $[\alpha]_D^{24}$ +8.6°(C = 2.12, ethanol)

(4) 3.20 g of d-1-(6-methoxycarbonylhexyl)-5-hydroxymethyl-2-pyrrolidone, 7.75 g of chrominium trioxide and 12.5 ml of pyridine are treated in the same manner as described in Example 2-(4). d-1-(6-Methoxycarbonylhexyl)-5-formyl-2-pyrrolidone is obtained as faintly yellow oil. Yield: 2.07 g $[\alpha]_D^{24.5}$ +2.2°(C = 2.25, ethanol)

EXAMPLE 5

(1) 143 mg of 65% sodium hydride in mineral oil are washed with n-hexane under a nitrogen gas atmosphere and suspended in 10 ml of dimethoxyethane. A solution of 875 mg of dimethyl 2-oxo-octylphosphonate in 5 ml of dimethoxyethane is added to the suspension under ice-cooling. Then, a solution of 930 mg of dl-1-(6-methoxycarbonylhexyl)-5-formyl-2-pyrrolidone in 5 ml of dimethoxyethane is added dropwise to the suspension under ice-cooling, and the mixture is stirred at room temperature for 2.5 hours. After the reaction, 60 ml of ether are added to the mixture. The mixture is washed with an aqueous solution saturated with ammonium sulfate, dried and then evaporated to remove solvent. The residue thus obtained is purified by thin layer chromatography [Silica gel, Solvent: ethylacetate-benzene (4:1)]. dl-20-Methyl-9,15-dioxo-13,14(trans)-didehydro-8-azaprostanoic acid methyl ester is obtained as pale yellow oil. Yield: 820 mg(63.5%)

IR spectrum $\gamma_{max.}^{liq.}(cm^{-1})$: 1735(ester), 1690(lactam), 1700 and 1635(enone)

NMR spectrum ppm(CDCl$_3$): 0.8–2.6(27H), 2.85–4.40(3H), 3.69(3H, S, —OCH$_3$), 6.30(1H, d, J = 16.2,

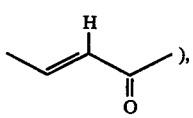), 6.67(1H, d of d, J = 16.2 and 7.4,

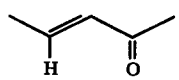

(2) 136 mg of sodium borohydride are added gradually to 45 ml of a methanol solution containing 820 mg of dl-20-methyl-9,15-dioxo-13,14(trans)-didehydro-8-azaprostanoic acid methyl ester. The addition is carried out under ice-cooling. The mixture is stirred at the same temperature for 20 minutes. After the reaction, the mixture is poured into ice-water. Then, the aqueous mixture is neutralized with ammonium sulfate-saturated 10% hydrochloric acid and extracted with 60 ml of ether. The ether layer is washed with an aqueous solution saturated with ammonium sulfate, dried and then evaporated to remove solvent. dl-20-Methyl-15ξ-hydroxy-13,14(trans)-didehydro-9-oxo-8-azaprostanoic acid methyl ester is obtained. Yield: 820 mg(99.5%)

The 8-azaprostanoate thus obtained is purified by silica gel column chromatography [Solvent: ethylacetate-benzenemethanol (6:2:1)], whereby dl-20-methyl-15α-hydroxy-13,14(trans)-didehydro-9-oxo-8-azaprostanoic acid methyl ester (140 mg) and dl-20-methyl-15β-hydroxy-13,14(trans)-didehydro-9-oxo-8-azaprostanoic acid methyl ester (109 mg) are obtained as colorless oil, respectively. The infrared absorption spectrum, nuclear magnetic resonance spectrum and Mass analysis of these compounds are identical to one another.

IR spectrum $\gamma_{max.}^{liq.}(cm^{-1})$: 3440(OH), 1735(ester), 1665(lactam)

NMR spectrum ppm(CDCl$_3$): 0.8–2.6(27H), 2.7–4.3(4H), 3.67(3H, S, O—CH$_3$), 5.53–5.72

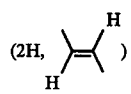

Mass analysis m/e: 367(M$^+$)

(3) One ml of an aqueous 20% sodium hydroxide solution is added to 1.5 ml of a methanol solution containing 110 mg of dl-20-methyl-15α-hydroxy-13,14(trans)-didehydro-9-oxo-8-azaprostanoic acid methyl ester. The addition is carried out under stirring and ice-cooling. The mixture is stirred at room temperature for 6 hours. After the reaction, the mixture is evaporated to remove solvent. The residue is diluted with a small amount of water, acidified with ammonium sulfate-saturated hydrochloric acid and extracted with 70 ml of ethylacetate. The extract is washed with water, dried and then evaporated to remove solvent. The crude product thus obtained is recrystallized from ethylacetate. dl-20-Methyl-15α-hydroxy-13,14(trans)-didehydro-9-oxo-8-azaprostanoic acid is obtained. Yield: 101.5 mg(96%). M.p. 110°–111° C.

IR spectrum $\gamma_{max.}^{nujol}(cm^{-1})$: 3150–2500(OH, COOH), 1725(COOH), 1660(lactam)

NMR spectrum ppm(CDCl$_3$): 0.8–2.5(27H), 2.8–4.3(4H), 5.55–5.74(2H,

Mass analysis m/e: 353 (M$^+$)

Analysis calculated for C$_{20}$H$_{35}$NO$_4$ C, 67.95; H, 9.98; N, 3.96 Found: C, 67.67; H, 9.90; N, 3.95

(4) 0.9 ml of an aqueous 20% sodium hydroxide solution and a solution of 81 mg of dl-20-methyl-15β-hydroxy-13,14(trans)-didehydro-9-oxo-8-azaprostanoic acid methyl ester in 1.5 ml of methanol are treated in the same manner as described in paragraph (3). The crude product is recrystallized from ethylacetate, whereby dl-20-methyl-15β-hydroxy-13,14(trans)-didehydro-9-oxo-8-azaprostanoic acid is obtained as colorless oil. Yield: 73.5 mg(95%) The infrared absorption spectrum, nuclear magnetic resonance spectrum and Mass analysis of this product are identical with those of the 15α-hydroxy compound obtained in paragraph (3).

EXAMPLE 6

(1) 937 mg of dl-1-(6-methoxycarbonylhexyl)-5-formyl-2-pyrrolidone, 150 mg of 65% sodium hydride, 803 mg of dimethyl 2-oxo-hexylphosphonate and 19.2 ml of dimethoxyethane are treated in the same manner as described in Example 5-(1). dl-20-Nor-9,15-dioxo-13,14(trans)-didehydro-8-azaprostanoic acid methyl ester is obtained as pale yellow oil. Yield: 622 mg (54%)

IR spectrum $\gamma_{max.}^{liq.}(cm^{-1})$: 1735(ester), 1690(lactam), 1675(enone)

NMR spectrum ppm(CDCl$_3$): 0.8–2.7(23H), 2.8–4.3(3H), 3.66(3H, S, O—CH$_3$), 6.17(1H, d, J = 1.62,

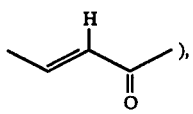

6.64(1H, d of d, J = 16.2 and 7.3,

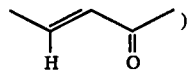

(2) 622 mg of dl-20-nor-9,15-dioxo-13,14(trans)-didehydro-8-azaprostanoic acid methyl ester, 112 mg of sodium borohydride and 52.5 ml of methanol are treated in the same manner as described in Example 5-(2). dl-20-Nor-15 ξ -hydroxy-13,14(trans)-didehydro-9-oxo-8-azaprostanoic acid methyl ester is obtained as pale yellow oil. Yield: 625 mg (99.2%)

The 8-azaprostanoate thus obtained is purified by silica gel chromatography [Solvent: ethylacetate-benzene(4:1)], whereby dl-20-nor-15α-hydroxy-13,14(trans)-didehydro-9-oxo-8-azaprostanoic acid methyl ester (189.5 mg) and dl-20-nor-15β-hydroxy-13,14(trans)-didehydro-9-oxo-8-azaprostanoic acid methyl ester (148 mg) are obtained as pale yellow oil, respectively. The infrared absorption spectrum, nuclear magnetic resonance spectrum and Mass analysis of these compounds are identical to one another.

IR spectrum
$\gamma_{max.}^{liq.}(cm^{-1})$; 3400(OH), 1735(ester), 1690(lactam)
NMR spectrum
ppm(CDCl$_3$): 0.92(3H, m, —C—CH$_3$), 1.15–2.64(20H), 2.67–4.35(4H), 3.70(3H, S, O—CH$_3$), 5.68(2H,

Mass analysis
m/e: 339(M+)

(3) 186.9 mg of dl-20-nor-15α-hydroxy-9-oxo-13,14(trans)-didehydro-8-azaprostanoic acid methyl ester, 1.4 ml of an aqueous 20% sodium hydroxide solution and 4 ml of methanol are treated in the same manner as described in Example 5-(3). dl-20-Nor-15α-hydroxy-13,14(trans)-didehydro-9-oxo-8-azaprostanoic acid is obtained. Yield: 179.1 mg(100%). M.p. 42°–44° C.

IR spectrum
$\gamma_{max.}^{liq.}(cm^{-1})$: 3300–2300(OH, COOH), 1725(COOH), 1660(lactam)
NMR spectrum
ppm(CDCl$_3$): 0.91(3H, C—CH$_3$), 1.1–2.5(20H), 2.85–4.35(4H), 5.66(2H,

Mass analysis
m/e: 325(M+)

(4) 138.9 mg of dl-20-nor-15β-hydroxy-13,14(trans)-didehydro-9-oxo-8-azaprostanoic acid methyl ester, one ml of an aqueous 20% sodium hydroxide solution and 3 ml of methanol are treated in the same manner as described in Example 5-(3). dl-20-Nor-15β-hydroxy-13,14(trans)-didehydro-9-oxo-8-azaprostanoic acid is obtained as pale yellow oil. Yield: 131.9 mg (99%). The infrared absorption spectrum, nuclear magnetic resonance spectrum and Mass analysis of this product are identical with those of the 15α-hydroxy compound obtained in paragraph (3).

EXAMPLE 7

(1) 296.5 mg of dl-1-(6-methoxycarbonylhexyl)-5-formyl-2-pyrrolidone, 47.3 mg of 65% sodium hydride, 30.6 mg of dimethyl 3,3-dimethyl-2-oxo-heptylphosphonate and 7 ml of dimethoxyethane are treated in the same manner as described in Example 5-(1). dl-16,16-Dimethyl-9,15-dioxo-13,14(trans)-didehydro-8-azaprostanoic acid methyl ester is obtained as yellow oil. Yield: 170 mg(38.7%)

IR spectrum
$\gamma_{max.}^{liq.}(cm^{-1})$: 1735(ester), 1690 and 1630(enone), 1680(lactam)
NMR spectrum
ppm(CDCl$_3$): 0.88(3H, m, —C—CH$_3$), 1.14(6H, S,

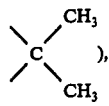

1.10–2.95(20H), 3.51–4.34(3H), 3.69(3H, S, —C—CH$_3$), 6.65 and 6.75(2H,

Mass analysis
m/e: 379(M+)

(2) 170 mg of dl-16,16-dimethyl-9,15-dioxo-13,14(trans)-didehydro-8-azaprostanoic acid methyl ester, 271 mg of sodium borohydride and 13 ml of methanol are treated in the same manner as described in Example 5-(2). dl-16,16-Dimethyl-15 ξ -hydroxy-13,14(trans)-didehydro-9-oxo-8-azaprostanoic acid methyl ester is obtained as yellow oil. Yield: 73.6 mg(43%)

IR spectrum
$\gamma_{max.}^{liq.}(cm^{-1})$: 3400(OH), 1735(ester), 1670(lactam)
NMR spectrum
ppm(CDCl$_3$): 0.86–3.05(29H), 3.33–4.30(4H), 3.68(3H, S, O—CH$_3$), 5.70(2H,

Mass analysis
m/e: 381(M+)

(3) 73 mg of dl-16,16-dimethyl-15 ξ -hydroxy-13,14(trans)-didehydro-9-oxo-8-azaprostanoic acid methyl ester, one ml of an aqueous 20% sodium hydroxide solution and 3 ml of methanol are treated in the same manner as described in Example 5-(3). dl-16,16-Dimethyl-15 ξ -hydroxy-13,14(trans)-didehydro-9-oxo-8-azaprostanoic acid is obtained as colorless oil. Yield: 70 mg (92%)

IR spectrum $\gamma_{max}^{liq.}(cm^{-1})$: 3400–2300(OH, COOH), 1720(COOH), 1670 (lactam)

NMR spectrum ppm(CDCl$_3$): 0.86(3H, m, C—CH$_3$), 0.88(6H, S,

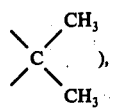

), 1.12–3.05(20H), 3.34–4.26(4H), 5.68 (2H,

)

Mass analysis m/e: 367(M$^+$)

EXAMPLE 8

(1) A solution of 291 mg of dl-20-methyl-9,15-dioxo-13,14(trans)-didehydro-8-azaprostanoic acid methyl ester in 9 ml of ether is added dropwise to an ether solution of methylmagnesium iodide (said methylmagnesium iodide solution being prepared from 566 mg of methyl iodide, 97 mg of magnesium and 6 ml of ether) at −20° C. under stirring in a nitrogen gas atmosphere. The mixture is stirred at the same temperature for one hour. Then, concentrated hydrochloric acid and an aqueous solution saturated with ammonium chloride are added to the mixture to decompose methylmagnesium iodide. After the ether layer is separated from the mixture, the aqueous layer is extracted with ethylacetate. The ethylacetate extract is combined with the ether layer obtained above. The combined solution is washed with an aqueous solution saturated with ammonium sulfate, dried and then evaporated to remove solvent. The residue thus obtained is purified by thin layer chromatography [Silica gel, Solvent: ethylacetatebenzene (4:1)]. dl-15 ξ,20-Dimethyl-15 ξ-hydroxy-13,14(trans)-didehydro-9-oxo-8-azaprostanoic acid methyl ester is obtained as colorless oil. Yield: 201 mg (66%)

IR spectrum $\gamma_{max}^{liq.}(cm^{-1})$: 3400(OH), 1735(esters), 1665(lactam)

NMR spectrum ppm(CDCl$_3$): 0.8–2.5(30H), 2.8–4.2(3H), 3.67(3H, S, O—CH$_3$), 5.50–5.68(2H, m,

)

Mass analysis m/e: 382(M$^+$ + 1), 363(M$^+$ — H$_2$O)

(2) 1.5 ml of an aqueous 20% sodium hydroxide solution are added to 4.5 ml of a methanol solution containing 151 mg of dl-15 ξ,20-dimethyl-15 ξ-hydroxy-13,14(trans)-didehydro-9-oxo-8-azaprostanoic acid methyl ester. The addition is carried out under ice-cooling. The mixture is stirred at room temperature for 6 hours. After the reaction, the mixture is evaporated to remove solvent. 5 ml of water are added to the residue, and the aqueous solution is acidified with concentrated hydrochloric acid. Then, the aqueous solution is saturated with ammonium sulfate and extracted with ethylacetate. The extract is washed with an aqueous solution saturated with ammonium sulfate, dried and then evaporated to remove solvent. dl-15 ξ,20-Dimethyl-15 ξ-hydroxy-13,14(trans)-didehydro-9-oxo-8-azaprostanoic acid is obtained as colorless oil. Yield: 135 mg (93.8%)

IR spectrum $\gamma_{max}^{liq.}(cm^{-1})$: 3350–2500(OH,COOH), 1720(COOH), 1660(lactam)

NMR spectrum ppm(CDCl$_3$): 0.7–2.5(20H), 2.8–4.2(3H), 5.48–5.66(2H, m,

)

Mass analysis m/e: 367(M$^+$), 349(M$^+$ — H$_2$O)

EXAMPLE 9

(1) 100 mg of dl-20-nor-1,15-dioxo-13,14(trans)-didehydro-8-azaprostanoic acid methyl ester, 36 mg of magnesium, 211 mg of methyl iodide and 8 ml of ether are treated in the same manner as described in Example 8-(1). dl-20-Nor-15 ξ-hydroxy-15 ξ-methyl-13,14(trans)-didehydro-9-oxo-8-azaprostanoic acid methyl ester is obtained as colorless oil. Yield: 54 mg (51.5%)

IR spectrum $\gamma_{max}^{liq.}(cm^{-1})$: 3400(OH), 1735(ester), 1665(lactam)

NMR spectrum ppm(CDCl$_3$): 0.8–2.5(26H), 2.85–4.20(3H), 3.67(3H, S, O—CH$_3$), 5.50–5.68

(2H, 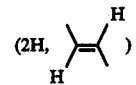 )

Mass analysis m/e: 353(M$^+$), 335(M$^+$ — H$_2$O)

(2) 50 mg of dl-20-nor-15 ξ-hydroxy-15 ξ-methyl-13,14(trans)-didehydro-9-oxo-8-azaprostanoic acid methyl ester, 0.5 ml of an aqueous 20% sodium hydroxide solution and 1.5 ml of methanol are treated in the same manner as described in Example 8-(2). dl-20-Nor-15 ξ-hydroxy-15 ξ-methyl-13,14(trans)-didehydro-9-oxo-8-azaprostanoic acid is obtained as colorless oil. Yield: 44 mg (91.7%)

IR spectrum $\gamma_{max}^{liq.}(cm^{-1})$: 3350–2500(OH, COOH), 1715(COOH), 1660(lactam)

NMR spectrum ppm(CDCl$_3$): 0.8–2.5(26H), 2.7–4.2(3H), 5.51–5.69(2H,

)

Mass analysis m/e: 339(M$^+$), 321(M$^+$ — H$_2$O)

EXAMPLE 10

(1) 205 mg of 65% sodium hydride are suspended in 33 ml of dimethoxyethane under a nitrogen gas atmosphere. A solution of 1.52 g of dimethyl 2-oxo-octylphosphonate in 6 ml of dimethoxyethane is added to the suspension under ice-cooling. The mixture is stirred at the same temperature for 10 minutes and at room temperature for 15 minutes. After the mixture is cooled in an ice-water bath, a solution of 1.49 g of l-1-(6-methoxycarbonylhexyl)-5-formyl-2-pyrrolidone in 6 ml of dimethoxyethane is added dropwise thereto, and the mixture is further stirred at the same temperature for one hour and at room temperature for 1.5 hours. 50 ml of ether are added to the mixture. Then, the mixture is washed with an aqueous solution saturated with ammonium sulfate, dried and evaporated to remove solvent. The residue thus obtained is purified by thin layer chromatography [Silica gel, Solvent: ethylacetate-benzene (6:1)]. l-20-Methyl-9,15-dioxo-13,14(trans)-didehydro-8-azaprostanoic acid methyl ester is obtained as faintly yellow oil. Yield: 1.49 g (71.6%)

(2) 0.24 g of sodium borohydride is added gradually to 60 ml of a methanol solution containing 1.45 g of l-20-methyl-9,15-dioxo-13,14(trans)-didehydro-8-azaprostanoic acid methyl ester. The addition is carried out under a nitrogen gas atmosphere and under cooling with chloroform-dry ice. The mixture is stirred at the same temperature for 50 minutes. After the reaction, the mixture is poured into 180 ml of ice-water. Then, the mixture is saturated with ammonium sulfate and extracted with ethylacetate. The extract is washed with an aqueous solution saturated with ammonium sulfate, dried and then evaporated to remove solvent. l-20-methyl-15 $\xi$-hydroxy-13,14(trans)-didehydro-9-oxo-8-azaprostanoic acid methyl ester is obtained. Yield: 1.35 g The 8-azaprostanoate thus obtained is purified by thin layer chromatography [Silica gel, Solvent: ethylacetate-benzene-methanol (8:1:1)], whereby l-20-methyl-15α-hydroxy-13,14(trans)-didehydro-9-oxo-8-azaprostanoic acid methyl ester (591 mg) and l-20-methyl-15β-hydroxy-13,14(trans)-didehydro-9-oxo-8-azaprostanoic acid methyl ester (661 mg) are obtained as colorless oil, respectively. Mass analysis of these compounds are identical to one another.
Mass analysis:
m/e: 367(M+)

(3) 5 ml of an aqueous 20% sodium hydroxide solution are added to 7.5 ml of a methanol solution containing 555 mg of l-20-methyl-15α-hydroxy-13,14(trans)-didehydro-9-oxo-8-azaprostanoic acid methyl ester. The addition is carried out under a nitrogen gas atmosphere and ice-cooling. The mixture is stirred at room temperature for 1.5 hours. After the reaction, the mixture is evaporated to remove solvent. The residue is acidified with concentrated hydrochloric acid under ice-cooling, and the resultant precipitate is collected by filtration. The precipitate is washed with water, dried and then recrystallized from ethylacetate. l-20-Methyl-15α-hydroxy-13,14(trans)-didehydro-9-oxo-8-azaprostanoic acid is obtained as colorless needles. Yield: 400 mg (75%) M.p. 114°–116° C. $[\alpha]_D^{25}$ −5.6°(C = 1.0, ethanol)
Mass analysis
m/e: 353(M+)

(4) 5.5 ml of an aqueous 20% sodium hydroxide solution, 598 mg of l-20-methyl-15β-hydroxy-13,14(trans)-didehydro-9-oxo-8-azaprostanoic acid methyl ester and 8.5 ml of methanol are treated in the same manner as described in paragraph (3). After the reaction, the mixture is evaporated to remove solvent. The residue is acidified with concentrated hydrochloric acid under ice-cooling and extracted with chloroform. The extract is dried and evaporated to remove solvent. Then, the residue thus obtained is recrystallized from ethylacetate. l-20-Methyl-15β-hydroxy-13,14(trans)-didehydro-9-oxo-8-azaprostanoic acid is obtained. Yield: 280 mg(48.7%) M.p. 82°–83° C. $[\alpha]_D^{27}$ −28.0°(C = 0.5, ethanol)

EXAMPLE 11

(1) 138 mg of 65% sodium hydride, 1.02 g of dimethyl 2-oxo-octylphosphonate, 1.0 g of d-1-(6-methoxycarbonylhexyl)-5-formyl-2-pyrrolidone and 30 ml of dimethoxyethane are treated in the same manner as described in Example 10-(1). d-20-Methyl-9,15-dioxo-13,14(trans)-didehydro-8-azaprostanoic acid methyl ester is obtained as faintly yellow oil. Yield: 1.05 g (73.2%)

(2) 955 mg of d-20-methyl-9,15-dioxo-13,14(trans)-didehydro-8-azaprostanoic acid methyl ester, 160 mg of sodium borohydride and 40 ml of methanol are treated in the same manner as described in Example 10-(2). d-20-Methyl-15 $\xi$-hydroxy-13,14(trans)-didehydro-9-oxo-8-azaprostanoic acid methyl ester is obtained. Yield: 950 mg.

The 8-azaprostanoate thus obtained is purified by thin layer chromatography [Silica gel, Solvent: ethylacetate-benzene-methanol (8:1:1)], whereby d-20-methyl-15α-hydroxy-13,14(trans)-didehydro-9-oxo-8-azaprostanoic acid methyl ester (386 mg) and d-20-methyl-15β-hydroxy-13,14(trans)-didehydro-9-oxo-8-azaprostanoic acid methyl ester (426 mg) are obtained as yellow oil, respectively. Mass analysis of these compounds are identical to one another.
Mass analysis
m/e: 367(M+)

(3) 348 mg of d-20-methyl-15α-hydroxy-13,14(trans)-didehydro-9-oxo-8-azaprostanoic acid methyl ester, 3 ml of an aqueous 20% sodium hydroxide solution and 4.5 ml of methanol are treated in the same manner as described in Example 10-(3). d-20-Methyl-15α-hydroxy-13,14(trans)-9-oxo-8-azaprostanoic acid is obtained as crystals. Yield: 231 mg (69%) M.p. 115°–117° C. $[\alpha]_D^{25}$ + 5.6°(C = 1.0, ethanol)

(4) 364 mg of d-20-methyl-15β-hydroxy-13,14(trans)-didehydro-9-oxo-8-azaprostanoic acid methyl ester, 3 ml of an aqueous 20% sodium hydroxide solution and 4.5 ml of methanol are treated in the same manner as described in Example 10-(3). d-20-Methyl-15β-hydroxy-13,14(trans)-didehydro-9-oxo-8-azaprostanoic acid is obtained as crystals. Yield: 192 mg (55%) M.p. 82°–84° C. $[\alpha]_D^{27}$ + 27.5°(C = 0.51, ethanol)
Mass analysis
m/e: 353(M+)

EXAMPLE 12

(1) 256.1 mg of 65% sodium hydride, 1.67 g of dimethyl 2-oxo-hexylphosphonate, 1.862 g of l-1-(6-methoxycarbonylhexyl)-5-formyl-2-pyrrolidone and 56 ml of dimethoxyethane are treated in the same manner as described in Example 10-(1). l-20-Nor-9,15-dioxo-13,14(trans)-didehydro-8-azaprostanoic acid methyl ester is obtained as yellow oil. Yield: 1.69 g (68%)

(2) 1.57 mg of l-20-nor-9,15-dioxo-13,14(trans)-didehydro-8-azaprostanoic acid methyl ester, 280 mg of sodium borohydride and 70 ml of methanol are treated in the same manner as described in Example 10-(2). l-20-Nor-15 $\xi$-hydroxy-13,14(trans)-didehydro-9-oxo-8-azaprostanoic acid methyl ester is obtained as colorless oil. Yield: 1.51 g The 8-azaprostanoate thus obtained is purified by thin layer chromatography [Silica gel, Solvent: ethylacetate-benzene (2:1)], whereby 1-20-nor-15α-hydroxy-13,14(trans)-didehydro-9-oxo-8-azaprostanoic acid methyl ester (600 mg) and 1-20-nor-15β-hydroxy-13,14(trans)-didehydro-9-oxo-8-azaprostanoic acid methyl ester (580 mg) are obtained, respectively. Mass analysis of these compounds are identical to one another.

Mass analysis
m/e: 339(M+)

(3) 384 mg of 1-20-nor-15α-hydroxy-13,14(trans)-didehydro-9-oxo-8-azaprostanoic acid methyl ester, 3 ml of an aqueous 20% sodium hydroxide solution and 6 ml of methanol are treated in the same manner as described in Example 1-(3). 1-20-Nor-15α-hydroxy-13,14(trans)-didehydro-9-oxo-8-azaprostanoic acid is obtained as crystals. Yield: 350 mg (95.3%) M.p. 55°–57° C. $[\alpha]_D^{29}$ −5.9°(C = 2.0, ethanol)

Mass analysis
m/e: 325(M+)

(4) 461.5 mg of 1-20-nor-15β-hydroxy-13,14(trans)-didehydro-9-oxo-8-azaprostanoic acid methyl ester, 3 ml of an aqueous 20% sodium hydroxide solution and 6 ml of methanol are treated in the same manner as described in Example 10-(4). 1-20-Nor-15β-hydroxy-13,14(trans)-didehydro-9-oxo-8-azaprostanoic acid is obtained as pale yellow oil. Yield: 353 mg (79.8%) $[\alpha]_D^{29}$ −26.3°(C = 2.0, ethanol)

Mass analysis
m/e: 325 (M+)

EXAMPLE 13

(1) 129 mg of 65% sodium hydride are suspended in 12 ml of dimethoxyethane under a nitrogen gas atmosphere. A solution of 875 mg of dimethyl 2-oxo-nonylphosphonate in 4 ml of dimethoxyethane is added to the suspension under ice-cooling. The mixture is stirred at the same temperature for 30 minutes. A solution of 850 mg of dl-1-(6-methoxycarbonylhexyl)-5-formyl-2-pyrrolidone in 4 ml of dimethoxyethane is added to the mixture, and said mixture is further stirred at the same temperature for 10 minutes and at room temperature for 2 days. An aqueous solution saturated with ammonium sulfate is added to the mixture. Then, the mixture is extracted twice with ether. The extract is washed with an aqueous solution saturated with ammonium sulfate, dried and then evaporated to remove solvent. The residue thus obtained is purified by thin layer chromatography [Silica gel, Solvent: ethylacetate-benzene (4:1)]. dl-20-Ethyl-9,15-dioxo-13,14(trans)-didehydro-8-azaprostanoic acid methyl ester is obtained. Yield: 667 mg (53%)

Mass analysis
m/e: 379 (M+)

(2) 0.199 g of sodium borohydride is added gradually to 95 ml of an absolute methanol solution containing 1.24 g of dl-20-ethyl-9,15-dioxo-13,14(trans)-didehydro-8-azaprostanoic acid methyl ester. The addition is carried out under a nitrogen gas atmosphere and under ice-cooling. The mixture is stirred at the same temperature for 2 hours. After the reaction, the mixture is adjusted to pH 4 with 10% hydrochloric acid and evaporated at about 40° C. to remove methanol. The residue thus obtained is mixed with an aqueous solution saturated with ammonium sulfate and then extracted four times with ether. The ether extract is washed with an aqueous solution saturated with ammonium sulfate, dried and evaporated to remove solvent. dl-20-Ethyl-15 ξ-hydroxy-13,14(trans)-didehydro-9-oxo-8-azaprostanoic acid methyl ester is obtained as an oil. Yield: 1.27 g.

The 8-azaprostanoate thus obtained is purified by thin layer chromatography [Silica gel, Solvent: ethylacetate-benzene (2:1)], whereby dl-20-ethyl-15α-hydroxy-13,14(trans)-didehydro-9-oxo-8-azaprostanoic acid methyl ester (244 mg) (M.p. 38°–40° C., recrystallized from petroleum ether) and dl-20-ethyl-15β-hydroxy-13,14(trans)-didehydro-9-oxo-8-azaprostanoic acid methyl ester (150 mg) (M.p. 27°–28° C., recrystallized from petroleum ether) are obtained as white powder, respectively. Mass analysis of these compounds are identical to one another.

Mass analysis
m/e: 387 (M+)

(3) 2 ml of an aqueous 20% sodium hydroxide solution are added to 3 ml of a methanol solution containing 234.7 mg of dl-20-ethyl-15α-hydroxy-13,14(trans)-didehydro-9-oxo-8-azaprostanoic acid methyl ester. The addition is carried out under a nitrogen gas atmosphere and ice-cooling. The mixture is stirred at room temperature for 2 hours. After the reaction, the mixture is evaporated to remove solvent. The residue is adjusted to pH 3 with hydrochloric acid under ice-cooling and then extracted with ethylacetate. The extract is washed with an aqueous solution saturated with ammonium sulfate, dried and then evaporated to remove solvent. The residue thus obtained is recrystallized from a mixture of ethylacetate and petroleum ether. dl-20-Ethyl-15α-hydroxy-13,14(trans)-didehydro-9-oxo-8-azaprostanoic acid is obtained as colorless crystals. Yield: 153 mg M.p. 74°–75° C.

(4) One ml of an aqueous 20% sodium hydroxide solution, 142.5 mg of dl-20-ethyl-15β-hydroxy-13,14(trans)-didehydro-9-oxo-8-azaprostanoic acid methyl ester and 2 ml of methanol are treated in the same manner as described in paragraph (3). dl-20-Ethyl-15β-hydroxy-13,14(trans)-didehydro-9-oxo-8-azaprostanoic acid is obtained as white fine needles. Yield: 100 mg M.p. 76°–77° C. (recrystallized from a mixture of ethylacetate and petroleum ether).

Mass analysis
m/e: 367 (M+)

EXAMPLE 14

(1) 297.1 mg of 65% sodium hydride, 2.33 g of dimethyl 2-oxo-nonylphosphonate, 2.16 g of 1-1-(6-methoxycarbonylhexyl)-5-formyl-2-pyrrolidone and 64 ml of dimethoxyethane are treated in the same manner as described in Example 10-(1). 1-20-Ethyl-9,15-dioxo-13,14(trans)-didehydro-8-azaprostanoic acid methyl ester is obtained as colorless oil. Yield: 2.275 g (70.9%)

(2) 2.275 mg of 1-20-ethyl-9,15-dioxo-13,14(trans)-didehydro-8-azaprostanoic acid methyl ester, 364 mg of sodium borohydride and 180 ml of methanol are treated in the same manner as described in Example 10-(2). 1-20-Ethyl-15 ξ-hydroxy-13,14(trans)-didehydro-9-oxo-8-azaprostanoic acid methyl ester is obtained. Yield: 2.20 g.

The 8-azaprostanoate thus obtained is purified by thin layer chromatography [Silica gel, Solvent: ethylacetate-benzene (2:1)], whereby 1-20-ethyl-15α-hydroxy-13,14(trans)-didehydro-9-oxo-8-azaprostanoic acid methyl ester (957 mg) and 1-20-ethyl-15β-hydroxy-13,14(trans)-didehydro-9-oxo-8-azaprostanoic acid methyl ester (965 mg) are obtained as crystals, respectively. M.p. 51°–52° C. (15α-isomer) and 40°–41° C. (15β-isomer). Mass analysis of these compounds are identical to one another.

Mass analysis
m/e: 381 (M+)

(3) 415 mg of 1-20-ethyl-15α-hydroxy-13,14(trans)-didehydro-9-oxo-8-azaprostanoic acid methyl ester, 3 ml of an aqueous 20% sodium hydroxide solution and 6 ml of methanol are treated in the same manner as described in Example 10-(3). 1-20-Ethyl-15α-hydroxy-13,14(trans)-didehydro-9-oxo-8-azaprostanoic acid is obtained as crystals. Yield: 336 mg M.p. 76°–77° C. $[\alpha]_D^{30}$ −4.4°(C = 1, ethanol)

Mass analysis
m/e: 367 (M+)

(4) 440 mg of 1-20-ethyl-15β-hydroxy-13,14(trans)-didehydro-9-oxo-8-azaprostanoic acid methyl ester, 3 ml of an aqueous 20% sodium hydroxide solution and 6 ml of methanol are treated in the same manner as described in Example 1-(4). 1-20-Ethyl-15β-hydroxy-13,14(trans)-didehydro-9-oxo-8-azaprostanoic acid is obtained as crystals. Yield: 342 mg. M.p. 60°–61° C. $[\alpha]_D^{30}$ −27.4°(C = 1, ethanol)

Mass analysis
m/e: 367 (M+)

EXAMPLE 15

(1) 224 mg of 65% sodium hydride, 1.856 g of dimethyl 2-oxo-decylphosphonate, 1.63 g of 1-1-(6-methoxycarbonylhexyl)-5-formyl-2-pyrrolidone and 49 ml of dimethoxyethane are treated in the same manner as described in Example 10-(1). 1-20-n-Propyl-9,15-dioxo-13,14(trans)-didehydro-8-azaprostanoic acid methyl ester is obtained. Yield: 1.556 g (62%)

(2) 1.556 g of 1-20-n-propyl-9,15-dioxo-13,14(trans)-didehydro-8-azaprostanoic acid methyl ester, 241 mg of sodium borohydride and 100 ml of methanol are treated in the same manner as described in Example 10-(2). 1-20-n-Propyl-15 ξ-hydroxy-13,14(trans)-didehydro-9-oxo-8-azaprostanoic acid methyl ester is obtained. Yield: 1.56 g.

The 8-azaprostanoate thus obtained is purified by thin layer chromatography [Silica gel, Solvent: ethylacetate-benzene (4:1)], whereby 1-20-n-propyl-15α-hydroxy-13,14(trans)-didehydro-9-oxo-8-azaprostanoic acid methyl ester (604 mg) (M.p. 37°–38° C.) and 1-20-n-propyl-15β-hydroxy-13,14(trans)-didehydro-9-oxo-8-azaprostanoic acid methyl ester (585.4 mg) (yellow oil) are obtained, respectively. Mass analysis of these compounds are identical to one another.

Mass analysis
m/e: 395 (M+)

(3) 523.5 mg of 1-20-n-propyl-15α-hydroxy-13,14(trans)-didehydro-9-oxo-8-azaprostanoic acid methyl ester, 3 ml of an aqueous 20% sodium hydroxide solution and 6 ml of methanol are treated in the same manner as described in Example 10-(3). 1-20-n-Propyl-15α-hydroxy-13,14(trans)-didehydro-9-oxo-8-azaprostanoic acid is obtained as yellow oil. Yield: 504 mg (100%) $[\alpha]_D^{28}$ −5.2°(C = 2, ethanol)

Mass analysis
m/e: 387 (M+)

EXAMPLE 16

(1) 0.165 mg of 65% sodium hydride, 1.437 g of dimethyl 2-oxo-undecylphosphonate, 1.2 g of 1-1-(6-methoxycarbonylhexyl)-5-formyl-2-pyrrolidone and 36 ml of dimethoxyethane are treated in the same manner as described in Example 10-(1). 1-20-n-Butyl-9,15-dioxo-13,14(trans)-didehydro-8-azaprostanoic acid methyl ester is obtained as yellow oil. Yield: 1.035 g (54%)

(2) One g of 1-20-n-butyl-9,15-dioxo-13,14(trans)-didehydro-8-azaprostanoic acid methyl ester, 150 mg of sodium borohydride and 70 ml of methanol are treated in the same manner as described in Example 10-(2). 1-20-n-Butyl-15 ξ -hydroxy-13,14(trans)-didehydro-9-oxo-8-azaprostanoic acid methyl ester is obtained. Yield: 990 mg.

The 8-azaprostanoate thus obtained is purified by thin layer chromatography [Silica gel, Solvent: ethylacetate-benzene (4:1)], whereby 1-20-n-butyl-15α-hydroxy-13,14(trans)-didehydro-9-oxo-8-azaprostanoic acid methyl ester (423 mg) (yellow oil) and 1-20-n-butyl-15β-hydroxy-13,14(trans)-didehydro-9-oxo-8-azaprostanoic acid methyl ester (426 mg) (M.p. 54°–55° C., recrystallized from ethylacetate-petroleum ether) are obtained, respectively. Mass analysis of these compounds are identical to one another.

Mass analysis
m/e: 409 (M+)

(3) 395 mg of 1-20-n-butyl-15α-hydroxy-13,14(trans)-didehydro-9-oxo-8-azaprostanoic acid methyl ester, 3 ml of an aqueous 20% sodium hydroxide solution and 6 ml of methanol are treated in the same manner as described in Example 10-(3). 1-20-n-Butyl-15α-hydroxy-13,14(trans)-didehydro-9-oxo-8-azaprostanoic acid is obtained as yellow oil. Yield: 370 mg (97%) $[\alpha]_D^{28}$ −4.2°(C = 1, ethanol)

Mass analysis
m/e: 395 (M+)

EXAMPLE 17

(1) 175 mg of 65% sodium hydroxide are suspended in 9 ml of dimethoxyethane under a nitrogen gas atmosphere. A solution of dimethyl 2-oxo-dodecylphosphonate in 5 ml of dimethoxyethane is added to the suspension under ice-cooling. The mixture is stirred at the same temperature for 10 minutes and at room temperature for one hour. A solution of 1.27 g of 1-1-(6-methoxycarbonylhexyl)-5-formyl-2-pyrrolidone in 5 ml of dimethoxyethane is added to the mixture, and said mixture is further stirred at room temperature for 2 hours. Ether is added to the mixture. Then, the mixture is washed with an aqueous solution saturated with ammonium sulfate, dried and evaporated to remove solvent. The residue thus obtained is purified by thin layer chromatography [Silica gel, Solvent: dichloroethane-ether (2:1)]. 1-20-n-Pentyl-9,15-dioxo-13,14(trans)-didehydro-8-azaprostanoic acid methyl ester is obtained as colorless oil. Yield: 1.012 g (2) 1.0127 g of 1-20-n-pentyl-9,15-dioxo-13,14(trans)-didehydro-8-azaprostanoic acid methyl ester, 0.1463 g of sodium borohydride and 70 ml of methanol are treated in the same manner as described in Example 10-(2). 1-20-n-Pentyl-15 ξ-hydroxy-13,14(trans)-didehydro-9-oxo-8-azaprostanoic acid methyl ester is obtained.

The 8-azaprostanoate thus obtained is purified by thin layer chromatography [Silica gel, Solvent: ethylacetate-benzene (4:1)], whereby 1-20-n-pentyl-15α-hydroxy-13,14(trans)-didehydro-9-oxo-8-azaprostanoic acid methyl ester (408.8 mg) (pale yellow oil) and 1-20-n-pentyl-15β-hydroxy-13,14(trans)-didehydro-9-oxo-8-azaprostanoic acid methyl ester (398.5 mg) (M.p. 59°–61° C.) are obtained, respectively. Mass analysis of these compounds are identical to one another.

Mass analysis m/e: 423 (M+)

(3) 400 mg. of 1-20-n-pentyl-15α-hydroxy-13,14(trans)-didehydro-9-oxo-8-azaprostanoic acid methyl ester, 3 ml of an aqueous 20% sodium hydroxide solution and 6 ml of methanol are treated in the same manner as described in Example 10-(3). l-20-n-Pentyl-15α-hydroxy-13,14(trans)-didehydro-9-oxo-8-azaprostanoic acid is obtained as colorless oil. Yield: 385 mg $[\alpha]_D^{28}$ —4.0°(C = 2, ethanol)

Mass analysis m/e: 409 (M+)

A preferred form of the present invention can be obtained when $R^1$ is ethyl or n-propyl, $R^2$ is hydrogen, and $R^3$ is hydrogen.

What we claim is:

1. A compound of the formula:

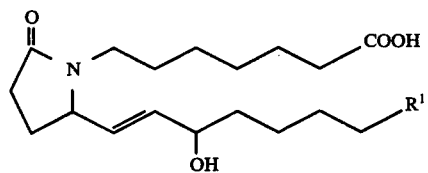

wherein $R^1$ is ethyl or n-propyl, or a pharmaceutically acceptable salt thereof.

2. The compound of claim 1 in which $R^1$ is ethyl.
3. The compound of claim 1 in which $R^1$ is n-propyl.
4. A racemic mixture of a 15α-isomer of the compound claimed in claim 1.
5. A laevo 15α-isomer of the compound claimed in claim 1.
6. The compound of claim 2 which is dl-20-methyl-15α-hydroxy-13,14(trans)-didehydro-9-oxo-8-azaprostanoic acid.
7. The compound of claim 2 which is l-20-methyl-15α-hydroxy-13,14(trans)-didehydro-9-oxo-8-azaprostanoic acid.
8. The compound of claim 3 which is dl-20-ethyl-15α-hydroxy-13,14(trans)-didehydro-9-oxo-8-azaprostanoic acid.
9. The compound of claim 3 which is l-20-ethyl-15α-hydroxy-13,14(trans)-didehydro-9-oxo-8-azaprostanoic acid.
10. The compound of claim 3 which is dl-20-ethyl-15β-hydroxy-13,14(trans)-didehydro-9-oxo-8-azaprostanoic acid.
11. The compound of claim 3 which is l-20-ethyl-15β-hydroxy-13,14(trans)-didehydro-9-oxo-8-azaprostanoic acid.
12. A pharmaceutical composition which comprises a therapeutically effective amount of a compound of the formula:

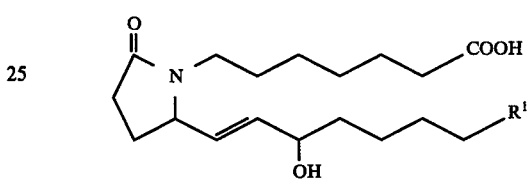

wherein $R^1$ is ethyl or n-propyl, or a pharmaceutically acceptable salt thereof, and a pharmaceutically acceptable carrier therefor.

* * * * *